United States Patent [19]

Wilson

[11] 4,106,502
[45] Aug. 15, 1978

[54] RESUSCITATOR

[75] Inventor: Porter C. Wilson, Tucson, Ariz.

[73] Assignee: Margaret M. Laurence, Arlington, Va.

[21] Appl. No.: 742,884

[22] Filed: Nov. 18, 1976

[51] Int. Cl.² ............................................. A61M 16/00
[52] U.S. Cl. ................................ 128/145.8; 128/145.7
[58] Field of Search ............... 128/145.8, 145.7, 145.6, 128/145.5, 142 R, 142.2, 145 A, 142.7, 140 R, 142.3; 137/102

[56] References Cited

U.S. PATENT DOCUMENTS

| 2,811,966 | 11/1957 | Hull ................................. 128/145.7 |
| 3,099,985 | 8/1963 | Wilson et al. ..................... 128/145.5 |
| 3,166,083 | 1/1965 | Girden ............................. 128/145 A |
| 3,814,091 | 6/1974 | Henkin ............................. 128/145.5 |

Primary Examiner—Robert W. Michell
Assistant Examiner—Henry J. Recla
Attorney, Agent, or Firm—Anthony DeLaurentis

[57] ABSTRACT

An improved apparatus for person to person, rescue breath function transfer for rendering artificial respiration which allows the operator to quickly and easily synchronize his breathing with that of the victim. The apparatus is provided with a flexible flutter valve to enable the operator to sense audibly and visually when the victim is exhaling and the relative amount of air he is exhaling. A by-pass valve enables the victim to inhale fresh air at any time he desires. The present invention may be adapted for rescue air sharing, booster breathing, and resuscitation in a toxic environment. A connector is provided for the quick connection of an air or oxygen tank to the fresh air inlet port. The apparatus of the present invention is designed to be lightweight, economical to fabricate, portable, and easy to clean or repair. A modified form of the present invention can be used for the artificial respiration of animals.

23 Claims, 9 Drawing Figures

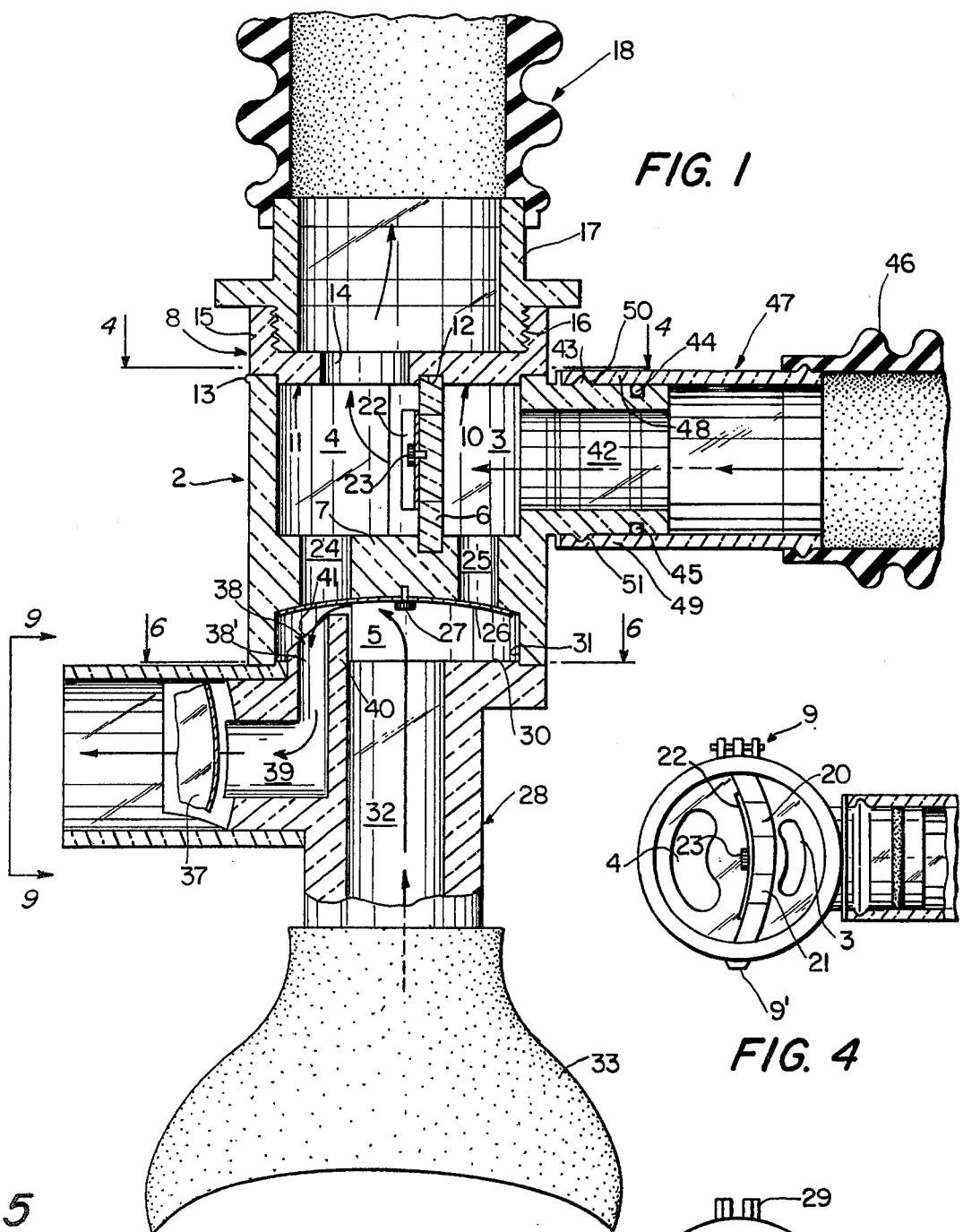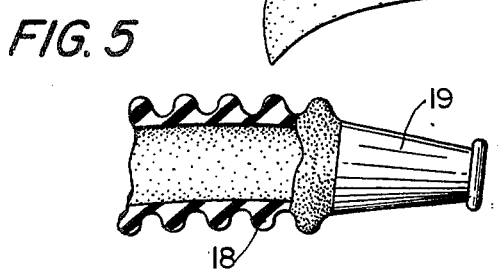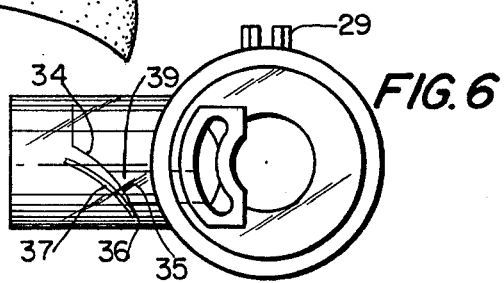

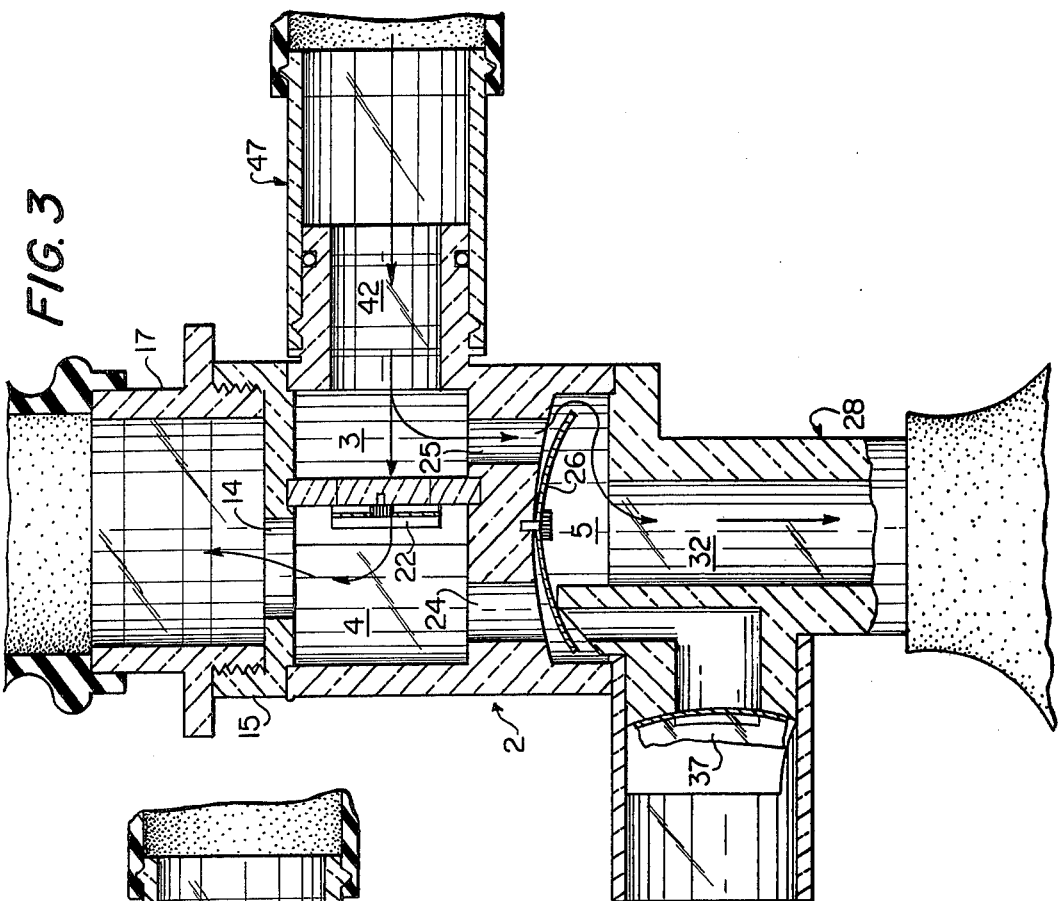
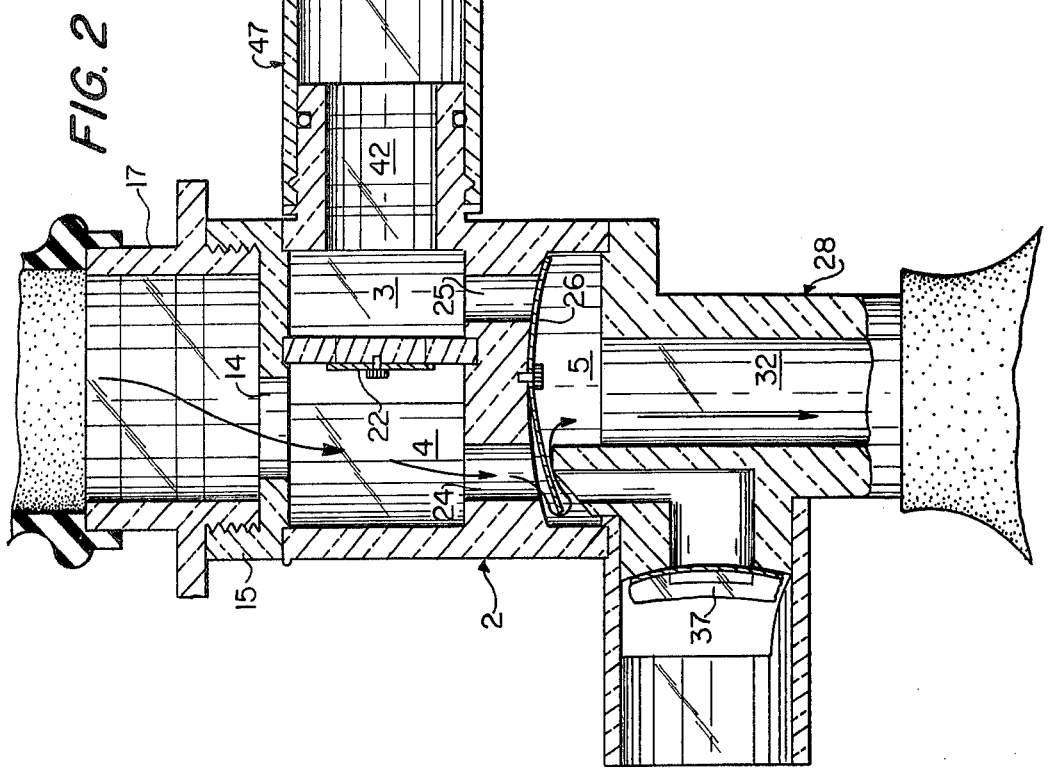

RESUSCITATOR

BACKGROUND OF THE INVENTION

This invention relates to resuscitators, but more particularly to a breath powered resuscitator, which insures tidal inflation of fresh unbreathed air to conscious, semi-conscious and unconscious victims experiencing difficulty in breathing, at the normal breathing rate and volume of air of the operator.

At the present time, mouth to mouth resuscitators on the market are simply gadgets which are not even reliable for the resuscitation function they are suppose to perform. They are usually cheap in construction and are psychologically ill conceived. While some resuscitators on the market may be somewhat effective on non-breathing and unconscious victims, they are totally unsuitable for semi-conscious and conscious victims. They do not allow the victim under the face mask to inhale at any time he wishes. When a person can't exhale they are usually willing to wait a few seconds, but when they can't inhale, that's when they panic and start ripping off the resuscitator, hampering the resuscitation he so badly needs.

Furthermore, resuscitators on the market have no way of determining when the victim is exhaling and if so, how much air is being exhaled. The only way an operator can determine if the victim is exhaling air is by visually observing the movements of the victim's chest or by listening very carefully for some breathing.

U.S. Pat. Nos. 3,018,775 and 3,099,985 disclose mouth to mouth resuscitators which are forerunners of the present invention, both of which are more involved, requiring some type of sliding valve, and are relatively expensive to manufacture. Further, neither resuscitator provides means for synchronizing breathing between the operator and the victim, nor are there any visible means provided to monitor the victim's exhalations. While U.S. Pat. No. 3,099,985 does disclose a bypass valve, which allows the victim to breath directly when desired, this bypass is designed mostly to allow direct inhalation by a victim sharing an air tank while in toxic environments.

SUMMARY OF THE INVENTION

The present invention comprises a simple, economical, lightweight, portable, efficient apparatus for use as in transferring the breathing function to victims who are unconscious, semi-conscious or conscious.

The present invention is designed for compact size, economical cost of fabrication, lightweight, internal visibility, ease of cleaning and repair. The body portion of the present invention is made of a clear plastic for lightweight and internal viewing. Both the top and bottom covers are secured to the body by means of a hinge which enables the covers to be quickly and easily opened, allowing easy accessibility to the interior for cleaning.

In accordance with one of the features of the present invention, means are provided for quickly and easily synchronizing the breathing between the operator and victim. A bypass valve is provided which allows the victim to inhale at any time he desires. Means are also provided wherein the operator can audibly and visually sense the exhalation of the victim. A thin film of plastic is placed over the exhalation outlet so that when the victim exhales the film of plastic will flutter, causing an audible noise which can be easily heard by the operator. Since the body of the present invention is made of a clear plastic, the fluttering plastic film can also be visually observed.

The present invention easily and quickly can be adopted for use in a toxic environment. Means are provided for the quick attachment or detachment of an air or oxygen supply tank to the air inlet of the present invention.

The above and other advantages and features of the present invention will become apparent on making reference to the specification to follow, the drawings and claims.

DESCRIPTION OF THE DRAWINGS

FIG. 1 is a cross sectional view of the present invention illustrating its configuration when an operator is in the inhalation phase and a victim is in the exhalation phase.

FIG. 2 is a cross sectional view of the present invention showing the operator exhalation and victim inhalation phase.

FIG. 3 is a cross sectional view of the present invention showing the victim bypass mode.

FIG. 4 is a cross sectional view of the present invention taken along line 4—4 of FIG. 1.

FIG. 5 is a plain view of a portion of the air exchange hose and operator mouth piece of the present invention.

FIG. 6 is a cross sectional view of the present invention taken along the line 6—6 of FIG. 1.

Like reference characters refer to like parts throughout the description of the drawings.

DESCRIPTION OF THE PREFERRED EMBODIMENT

Figure 7:
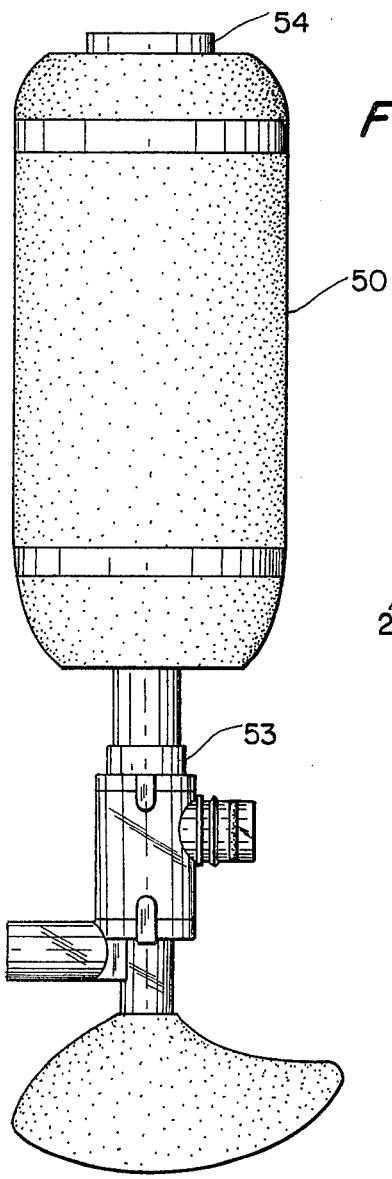
FIG. 7 is a plain view of a modified form of the present invention.

Referring to FIGS. 1, 2 and 3, a preferred embodiment of the present invention is shown comprising a cylindrical body 2 having chambers 3, 4, and 5 separated by walls 6 and 7. In the preferred embodiment body 2 is made of a clear plastic capable of being subjected to sterilization processes.

Mounted on top of body 2 and covering chambers 3 and 4 is snap cap cover 8 secured to body 2 by means of hinge 9 (see FIG. 4). Cover 8 has ridge sections 10 and 11 which form channel or groove 12. When the cover 8 is in the closed position ridge sections frictionally engage the inside walls of body 2, the top of wall 6 engaging channel 12. Integrally formed on the outer edge of snap cover 8, opposite hinge 9, is latch 9' which frictionally engages lip 13 on body 2. Cover 8 has a passage 14 connecting chamber 4 with air exchange hose 18. Integrally formed on the top of cover 8 is an annular wall 15. The interior of wall 15 has threads 16 to engage connector 17 attached to exchange hose 18. The other end of hose 18 is attached to mouth piece 19 (see FIG. 5) into which the operator breaths. While the preferred embodiment discloses the use of an air exchange hose an air exchange chamber 50 may be substituted (FIG. 7) which will be discussed more fully later.

Air passages 20 and 21 (FIG. 4) are formed in wall 6 connecting chambers 3 and 4 and flexible lexan flutter valve 22 is secured at 23 on the central portion of the wall 6 and is arranged to be opened upon inhalation of the operator. The side of wall 6 facing chamber 4, the same side on which valve 22 is placed, is concave in shape (see FIG. 4). This causes valve 22 to exert a small force against wall 6, preventing air from escaping to the atmosphere when the operator exhales and from letting unwanted air from prematurely entering chamber 4. Air passages 24 and 25 are formed in wall 7 connecting chambers 3 and 4 to chamber 5 and a flexible lexan flutter valve 26 is secured at 27 on central portion of the wall 7. The side of wall 7 which faces chamber 5, the same side on which valve 26 is placed, is concave in shape. In the same manner as valve 22, valve 26 is firmly held against wall 7. While valve 26 is described as one valve, it actually acts as two valves, so that passage 24 will open upon exhalation of the operator (see FIG. 2) and passage 25 will open upon the inhalation of the victim (see FIG. 3), both acting separately and independently of each other. In the preferred embodiment valves 22 and 26 are made of lexan sheet .005 inches, however, valves 22 and 26 are not limited to one specific material or size.

Figure 9:
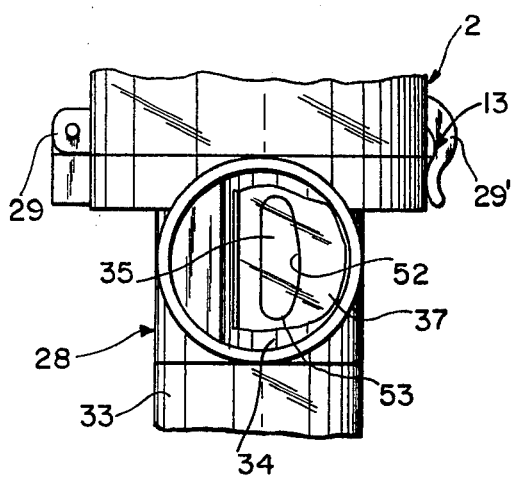
FIG. 9 is a side elevational view of a portion of the present invention illustrating the exhalation port thereof.

Mounted on the bottom of body 2 is snap cover 28 secured to body 2 by means of hinge 29 and latch 29'. Snap cover 28 has a slightly raised step 30 designed to fricitionally engage the inside wall 31 of body 2 sealing chamber 5 from the environment. Centrally located inhalation exhalation port or passage 32 connects chamber 5 to victim inhalation means or oral nasal mask 33. Cover 28 is provided with an exhalation inlet port 38. Passageway 38' connects inlet port 38 to an exhalation oulet port 39. Outlet port 39 has curved surface 34 (see FIG. 6) having an opening 35. Placed across opening 35 and secured at one side portion 36 of the curved surface 34 and along the side edge 52 of opening 35 is a thin lexan film 37 (see FIG. 9). When the victim exhales, air passes through port 39 causing film 37 to flutter producing an audible noise. The valve will flutter in proportion to the amount of air exhaled by the victim. Since the cover 28 and port 39 are also made of clear plastic, the fluttering of film 37 can be observed visually. Port 38 of column 40 is disposed directly below passage 24. The configuration of port 38 is such that when the flap of valve 26 is caused to open, flutter valve 26 will close off port 38 so that no air will escape to the atmosphere. The surface 41 of port 38 is inclined at such an angle so that when passage 24 is opened, valve 26 will lay substantially flat against face 41 covering the entire port 38.

Chamber 3 is provided with an air inlet passage 42. Integrally formed on passage 42 is an annular ridge 43 and groove 44. Placed in groove 44 is O-ring 45. In normal use air is merely drawn from the atmosphere into chamber 3. However, when bottled air or pure oxygen is desired, for example in a toxic environment, an optional snap on hose 46 connected to an air or oxygen tank (not shown) is attached to inlet passage 42. Hose 46 is secured to inlet passage 42 by means of snap on-pull off swivel connector 47 having clasps 48 and 49. Clasps 48 and 49 have recesses 51 and 50 which engage ridge 43. When an oxygen or air tank is desired, hose 46 is quickly attached to inlet 42 by simply pushing connector 47 so that clasps 48 and 49 deform slightly until ridge 43 engages grooves 50 and 51. O-ring 45 is slightly deformed against the inside wall of connector 47 forming an air tight seal.

A modified form of the present invention is shown in FIG. 7, wherein an air exchange hose 18 is replaced by exchange chamber 50. Integrally formed in chamber 50 is connector 53 which threads into annular wall 15 and mouth piece section 54. This modified form works in the same manner as the preferred embodiment except instead of the operator breathing into mouth piece 18, he now breathes into section 54.

In operation of the apparatus, inhalation by the operator and exhalation of the victim is shown in FIG. 1, the arrows representing the path of air flow. Inhalation by the operator through mouth piece 19 causes flap valve 22 to leave wall 6, opening passages 20 and 21 allowing fresh air to be drawn into air exchange hose 18. The operator then exhales exchanging air from hose into the victim, as is shown in FIG. 2, causing valve 22 to be forced against wall 6 thereby automatically closing passages 20 and 21. Left half of valve 26 is forced open against surface 41, closing port 38, the air passing through passage 24 through oral-nasal mask 33 into the victim. After the operator has finished exhaling valve 26 returns to its normal state against wall 7. During the victim exhalation phase, while operator again inhales, air passes from the victim through passage 38', out opening 35 and past fluttering film 37.

The victim may also inhale directly at any time during the operator inhalation phase, bypassing all other air flow. The inhalation of the victim will cause the right half of valve 26 below passage 25 to leave wall 7 (see FIG. 3) opening passage 25, forming a direct passage from the air source to the victim. Since the victim may breath at any time desired and the operator can easily determine when the victim is exhaling, synchronization between the breathing of the operator and victim is quickly and easily accomplished. When used in toxic air or underwater this feature also allows sharing of an air tank, or gas mask. The rescuer need not remove his face mask and eye protection. The described unit is simply connected so rescuer exhalation exits near his mouth. This rescuer exhalation port can be closed to shunt operator exhalation downward for resuscitation or booster breathing if needed by the victim.

Figure 8:
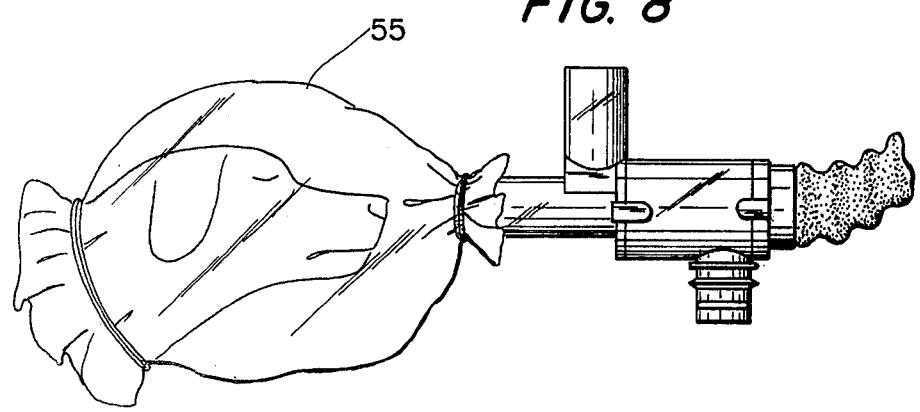
FIG. 8 is a plain view of a second modified form of the present invention.

FIG. 8 shows a modified form of the present invention which can be used in the veterinary field to assist the breathing of animals. A plastic air bag 55 is substituted for the face mask 33. Bag 55 is placed over the head of the animal, or in the case of small animals the animal may simply be placed inside the bag. The apparatus is then used in the same manner as previously described.

While the apparatus herein described is the preferred embodiment of the invention, it is to be understood that the invention is not limited to the precise form of apparatus, that changes may be made therein without departing from the scope of the invention which is defined in the appended claims.

I claim:

1. A mouth to mouth resuscitator for rendering artificial respiration by forcing tidal breaths of air into a victim comprising:
   a resuscitator body unit having a top portion, a bottom portion and exterior side wall means;
   top cover means adapted to sealingly engage said top portion of said body unit, said top cover means having an opening therethrough;
   bottom cover means adapted to sealingly engage said bottom portion of said body unit;
   said body unit further having first and second interior wall means, said interior wall means together with said top cover means, said bottom cover means and said exterior wall means defining within said body unit a fresh air inlet chamber, an air exchange chamber, and a victim inhalation chamber;

said fresh air inlet chamber being defined by said first interior wall means, said second interior wall means, said top cover means and a first portion of said exterior side wall means;

said air exchange chamber being defined by said first interior wall means, said second interior wall means, said top cover means and a second portion of said exterior side wall means;

said victim inhalation chamber being defined by said second interior wall means, said bottom cover means and a third portion of said exterior side wall means;

said exterior side wall means having an air inlet means connected thereto, said air inlet means having an inlet port therethrough, said inlet port opening into said fresh air inlet chamber and externally of said body unit;

said first interior wall means having an operator inhalation passage therethrough, said operator inhalation passage interconnecting said fresh air inlet chamber and said air exchange chamber;

first flap valve means for preventing flow through said operator inhalation passage from said air exchange chamber to said fresh air inlet chamber;

said second interior wall means having an operator exhalation passage therethrough, said operator exhalation passage interconnecting said air exchange chamber and said victim inhalation chamber;

second flap valve means for preventing flow through said operator exhalation passage from said victim inhalation chamber to said air exchange chamber, said operator exhalation passage being opened by the exhalation of the operator;

air exchange hose means having a first end thereof attached to said top cover means, said air exchange hose means communicating with said air exchange chamber through said opening in said top cover means, the free end of said hose means having a mouthpiece into which the operator breathes;

face mask means attached to said bottom cover means;

said bottom cover means having an exterior wall means and an interior wall means, said interior wall means and a first portion of said exterior wall means defining a connecting passage which interconnects said victim inhalation chamber and said face mask means;

said interior wall means and a second portion of said exterior wall means of said bottom cover means defining an exhalation passage, said exhalation passage terminating at one end thereof at an exhalation port formed through said exterior wall means and at the other end thereof at an exhalation intake port disposed adjacent to said operator exhalation passage such that when said second flap valve means is opened by the exhalation of the operator said second flap valve means closes said exhalation intake port, said exhalation port opening externally of said body unit and being in fluid communication with said victim inhalation chamber except when said exhalation intake port is closed by said second flap valve means;

a by-pass passage interconnecting said fresh air inlet chamber and said victim inhalation chamber; and third valve means permitting flow through said by-pass chamber from said fresh air inlet chamber to said victim inhalation chamber upon inhalation of the victim at any desired time;

whereby inhalation of the operator on said mouthpiece causes said first flap valve to open thus allowing fresh air to be drawn into said body unit through said inlet port, said air passing through said fresh air inlet chamber, said operator inhalation passage, said air exchange chamber and then through said air exchange hose means;

whereby exhalation of the operator causes said first flap valve means to close so as to close said operator inhalation passage and further causes said second flap valve means to open so as to open said operator exhalation passage and so as to close said exhalation intake port, thereby allowing air to pass from said air exchange hose means and into said face mask means through said air exchange chamber, said operator exhalation passage, said victim inhalation chamber and said connecting passage; and whereby exhalation of the victim causes said second flap valve means to close said operator exhalation passage and to open said exhalation intake port, thereby allowing the victim's exhalation to pass out of said body unit through said connecting passage, said victim inhalation chamber, said exhalation intake port, said exhalation passage and said exhalation port.

2. The apparatus according to claim 1, wherein said second and third flap valve means comprise a single flexible valve means mounted to said second interior wall means such that a first portion of said flexible valve means normally closes said operator exhalation passage and a second portion of said flexible valve means normally closes said by-pass passage, said first and second portions of said flexible flap valve opening and closing said operator exhalation passage and said by-pass passage independently of each other, said by-pass passage being opened by the inhalation of the victim, and said operator exhalation passage being opened by the exhalation of the operator.

3. The apparatus according to claim 2, wherein a thin film of plastic material is secured to said exterior wall means of said bottom cover means at the termination of said exhalation port, the surface of said wall means being shaped so that when air passes through said exhalation port said film of plastic material will be caused to flutter, thereby producing an audible indication of the victim's exhalation.

4. The apparatus according to claim 1, wherein a thin film of plastic material is secured to said exterior wall means of said bottom cover means at the termination of said exhalation port, the surface of said wall means being shaped so that when air passes through said exhalation port said film of plastic material will be caused to flutter, thereby producing an audible indication of the victim's exhalation.

5. The apparatus according to claim 4 wherein said means comprising said exhalation port is transparent such that the fluttering of said thin film of plastic can be sensed visually as well as audibly.

6. The apparatus according to claim 4, wherein said air inlet means includes an annular ridge portion and an annular groove in which an O-ring is placed.

7. The apparatus according to claim 1, wherein said air inlet means includes an annular ridge portion and an annular groove in which an O-ring is placed.

8. The apparatus of claim 7, further including:
a hose having a first end adapted to be connected to a contained source of air or oxygen; and
a snap-on pull-off connector attached to the other end of said hose, said connector having an inside wall and a plurality of clasps, said clasps having a groove such that upon connection of said connector to said air inlet means said groove engages said ridge portion on said air inlet means and said O-ring engages said inside wall of said connector.

9. A mouth to mouth resuscitator for rendering artificial respiration by forcing tidal breaths of air into a victim comprising:
a resuscitator body unit having a top portion, a bottom portion and exterior side wall means;
top cover means adapted to sealingly engage said top portion of said body unit, said top cover means having an opening therethrough;
bottom cover means adapted to sealingly engage said bottom portion of said body unit;
said body unit further having first and second interior wall means, said interior wall means together with said top cover means, said bottom cover means and said exterior wall means defining within said body unit a fresh air inlet chamber, a first air exchange chamber, and a victim inhalation chamber;
said fresh air inlet chamber being defined by said first interior wall means, said second interior wall means, said top cover means and a first portion of said exterior wall means;
said first air exchange chamber being defined by said first interior wall means, said second interior wall means, said top cover means and a second portion of said exterior side wall means;
said victim inhalation chamber being defined by said second interior wall means, said bottom cover means and a third portion of said exterior side wall means;
said exterior side wall means having an air inlet means connected thereto, said air inlet means having an inlet port therethrough, said inlet port opening into said fresh air inlet chamber and externally of said body unit;
said first interior wall means having an operator inhalation passage therethrough; said operator inhalation passage interconnecting said fresh air inlet chamber and said first air exchange chamber;
first flap valve means for preventing flow through said operator inhalation passage from said first air exchange chamber to said fresh air inlet chamber;
said second interior wall means having an operator exhalation passage therethrough, said operator exhalation passage interconnecting said first air exchange chamber and said victim inhalation chamber;
second flap valve means for preventing flow through said operator exhalation passage from said victim inhalation chamber to said first air exchange chamber, said operator exhalation passage being opened by the exhalation of the operator;
second air exchange chamber means having a first end thereof attached to said top cover means, said second air exchange chamber means communicating with said first air exchange chamber through said opening in said top cover means, the free end of the said second air exchange chamber means having mouthpiece means into which the operator breathes;
face mask means attached to said bottom cover means;
said bottom cover means having an exterior wall means and an interior wall means, said interior wall means and a first portion of said exterior wall means defining a connecting passage which interconnects said victim inhalation chamber and said face mask means;
said interior wall means and a second portion of said exterior wall means of said bottom cover means defining an exhalation passage, said exhalation passage terminating at one end thereof at an exhalation port formed through said exterior wall means and at the other end thereof at an exhalation intake port disposed adjacent to said operator exhalation passage such that when said second flap valve means is opened by the exhalation of the operator said second flap valve means closes said exhalation intake port, said exhalation port opening externally of said body unit and being in fluid communication with said victim inhalation chamber except when said exhalation intake port is closed by said second flap valve means;
a by-pass passage interconnecting said fresh air inlet chamber and said victim inhalation chamber; and
third valve means permitting flow through said by-pass passage from said fresh air inlet chamber to said victim inhalation chamber upon inhalation of the victim at any desired time;
whereby inhalation of the operator on said mouthpiece causes said first flap valve means to open thus allowing fresh air to be drawn into said body unit through said inlet port, said air passing through said fresh air inlet chamber, said operator inhalation passage, said first air exchange chamber and then through said second air exchange chamber means;
whereby exhalation of the operator causes said first flap valve means to close so as to close said operator inhalation passage and further causes said second flap valve means to open so as to open said operator exhalation passage and so as to close said exhalation intake port, thereby allowing air to pass from said second air exchange chamber means and into said face mask through said first air exchange chamber, said operator exhalation passage, said victim inhalation chamber and said connecting passage; and
whereby exhalation of the victim causes said second flap valve means to close said operator exhalation passage and to open said exhalation intake port, thereby allowing the victim's exhalation to pass out of said body unit through said connecting passage, said victim inhalation chamber, said exhalation intake port, said exhalation passage and said exhalation port.

10. The apparatus according to claim 9, wherein a thin film of plastic material is secured to said exterior wall means of said bottom cover means at the termination of said exhalation port, the surface of said wall means being shaped so that when air passes through said exhalation port said film of plastic material will be caused to flutter, thereby producing an audible indication of the victim's exhalation.

11. The apparatus according to claim 10 wherein said means comprising said exhalation port is transparent such that the fluttering of said thin film of plastic can be sensed visually as well as audibly.

12. The apparatus of claim 11, further including:
a hose having a first end adapted to be connected to a contained source of air or oxygen; and
a snap-on pull-off connector attached to the other end of said hose, said connector having an inside wall and a plurality of clasps, said clasps having a groove such that upon connection of said connector to said air inlet means said groove engages said ridge portion on said air inlet means and said O-ring engages said inside wall of said connector.

13. The apparatus according to claim 10, wherein said air inlet means includes an annular ridge portion and an annular groove in which an O-ring is placed.

14. A mouth to mouth resuscitator for rendering artificial respiration by forcing tidal breaths of air into a victim comprising:
a resuscitator body unit having a top portion, a bottom portion and exterior side wall means;
top cover means adapted to sealingly engage said top portion of said body unit, said top cover means having an opening therethrough;
bottom cover means adapted to sealingly engage said top portion of said body unit, said top cover means having an opening therethrough;
bottom cover means adapted to sealingly engage said bottom portion of said body unit;
said body unit further having first and second interior wall means, said interior wall means together with said top cover means said bottom cover means and said exterior wall means defining within said body unit a fresh air inlet chamber, an air exchange chamber, and a victim inhalation chamber;
said fresh air inlet chamber being defined by said first interior wall means, said second interior wall means, said top cover means and a first portion of said exterior side wall means;
said air exchange chamber being defined by said first interior wall means, said second interior wall means, said top cover means and a second portion of said exterior side wall means;
said victim inhalation chamber being defined by said second interior wall means, said bottom cover means and a third portion of said exterior side wall means;
said exterior side wall means having an air inlet means connected thereto, said air inlet means having an inlet port therethrough, said inlet port opening into said fresh air inlet chamber and externally of said body unit;
said first interior wall means having an operator inhalation passage therethrough said operator inhalation passage interconnecting said fresh air inlet chamber and said air exchange chamber;
first flap valve means for preventing flow through said operator inhalation passage from said air exchange chamber to said fresh air inlet chamber;
said second interior wall means having an operator exhalation passage therethrough, said operator exhalation passage interconnecting said air exchange chamber and said victim inhalation chamber;
second flap valve means for preventing flow through said operator exhalation passage from said victim inhalation chamber to said air exchange chamber, said operator exhalation passage being opened by the exhalation of the operator;
air exchange hose means having a first end thereof attached to said top cover means, said air exchange hose means communicating with said air exchange chamber through said opening in said top cover means, the free end of said hose means having a mouthpiece into which the operator breathes;
air bag means attached to said bottom cover means, said air bag means being adapted to receive the head of an animal or the entire animal;
said bottom cover means having an exterior wall means and an interior wall means, said interior wall means and a first portion of said exterior wall means defining a connecting passage which interconnects said victim inhalation chamber and said air bag means;
said interior wall means and a second portion of said exterior wall means of said bottom cover means defining an exhalation passage, said exhalation passage terminating at one end thereof at an exhalation port formed through said exterior wall means and at the other end thereof at an exhalation intake port disposed adjacent to said operator exhalation passage such that when said second flap valve means is opened by the exhalation of the operator said second flap valve means closes said exhalation intake port, said exhalation port opening externally of said body unit and being in fluid communication with said victim inhalation chamber except when said exhalation intake port is closed by said second flap valve means;
a by-pass passage interconnecting said fresh air inlet chamber and said victim inhalation chamber; and
third valve means permitting flow through said by-pass passage from said fresh air inlet chamber to said victim inhalation chamber upon inhalation of the victim at any desired time;
whereby inhalation of the operator on said mouthpiece causes said first flap valve means to open thus allowing fresh air to be drawn into said body unit through said inlet port, said air passing through said fresh air inlet chamber, said operator inhalation passage, said air exchange chamber and then through said air exchange hose means;
whereby exhalation of the operator causes said first flap valve means to close so as to close said operator inhalation passage and further causes said second flap valve means to open so as to open said operator exhalation passage and so as to close said exhalation intake port, thereby allowing air to pass from said air exchange hose means and into said air bag means through said air exchange chamber, said operator exhalation passage, said victim inhalation chamber and said connecting passage; and
whereby exhalation of the victim causes said second flap valve means to close said operator exhalation passage and to open said exhalation intake port, thereby allowing the victim's exhalation to pass out of said body unit through said connecting passage, said victim inhalation chamber, said exhalation intake port, said exhalation passage and said exhalation port.

15. The apparatus according to claim 14, wherein a thin film of plastic material is secured to said exterior wall means of said bottom cover means at the termination of said exhalation port, the surface of said wall means being shaped so that when air passes through said exhalation port said film of plastic material will be caused to flutter, thereby producing an audible indication of the victim's exhalation.

16. The apparatus according to claim 15, wherein said air inlet means includes an annular ridge portion and an annular groove in which an O-ring is placed.

17. The apparatus of claim 16, further including:
a hose having a first end adapted to be connected to a contained source of air or oxygen; and
a snap-on pull-off connector attached to the other end of said hose, said connector having an inside wall and a plurality of clasps, said clasps having a groove such that upon connection of said connector to said air inlet means said groove engages said ridge portion on said air inlet means and said O-ring engages said inside wall of said connector.

18. In a mouth to mouth resuscitator for rendering artificial respiration by forcing tidal breaths of air or oxygen into the lungs of a victim, the improvement which comprises:
a resuscitator body unit comprising top cover means, bottom cover means, and interconnecting wall means, said cover means and wall means defining a fresh air inlet chamber, an air exchange chamber, and a victim inhalation chamber;
said wall means having an operator inhalation passage for establishing fluid communication between said fresh air inlet chamber and said air exchange chamber;
a first flap valve normally closing said operator inhalation passage, said first valve being opened by the inhalation of an operator;
said wall means having an operator exhalation passage for establishing fluid communication between said air exchange chamber and said victim inhalation chamber;
a second flap valve normally closing said operator exhalation passage;
said second valve being actuated to open said operator exhalation passage by the exhalation of the operator;
said top cover means being adapted for connection to an air exchange means which is to be breathed into by the operator, and said top cover means having a port therethrough for establishing fluid communication between said air exchange chamber and the air exchange means;
said bottom cover being adapted for connection to victim inhalation means which is to be breathed into by the victim, said bottom cover means having an inhalation-exhalation port for establishing fluid communication between said victim inhalation chamber and the victim inhalation means, and an outlet port for exhausting victim exhalation, said outlet port being disposed relative to said second flap valve such that said outlet port is closed by said second flap valve upon operator exhalation;
means mounted to said bottom cover means and comprising an exhalation port in fluid communication with said outlet port;
said wall means of said resuscitator body unit being provided with a by-pass passage for establishing fluid communication between said fresh air inlet chamber and said victim inhalation chamber and a third flap valve normally closing said by-pass passage, said third valve being actuated to open by-pass passage by the inhalation of a victim any time the victim inhales;
said fresh air inlet chamber having an inlet port for establishing fluid communication between said fresh air inlet chamber and the fluid to be breathed by the victim, whereby upon inhalation of the operator on the air exchange means said first valve opens allowing the fluid to be breathed by the victim to be drawn through said inlet port into said fresh air inlet chamber, through said operator inhalation passage into said air exchange chamber, through said port in said top cover means into said air exchange means, and into the lungs of the operator, and whereupon exhalation of the operator said first valve closes said operator inhalation passage and said second valve opens said operator exhalation passage while closing said outlet port, thus causing operator exhalation to flow through the air exchange means into and through the air exchange means into and through said air exchange chamber, said operator exhalation passage, said victim inhalation means, and into the lungs of the victim, and whereupon exhalation of the victim said second valve is actuated to open said outlet port such that the victim exhalation passes through said victim inhalation means, said victim inhalation chamber, said outlet port and out of said unit through said exhalation port.

19. The improvement of claim 18 wherein said second and third flap valves comprise a single flexible valve means mounted to said wall means of said resuscitator body unit such that a first portion of said flexible valve means normally closes said operator exhalation passage and a second portion thereof normally closes said by-pass passage, said first and second portions opening and closing said exhalation passage and said by-pass passage independently of each other, said by-pass passage being opened by the inhalation of the victim and said operator exhalation passage being opened by the exhalation of the operator.

20. The improvement of claim 19, wherein said means comprising said exhalation port further comprises means for audibly sensing exhalation of the victim, said sensing means comprising a thin film of plastic placed across said exhalation port and secured thereto so as to flutter and produce an audible sound when victim exhalation passes through said port.

21. The improvement of claim 20, wherein said means comprising said exhalation port is transparent such that the fluttering of said thin film of plastic can be sensed visably as well as audibly.

22. The improvement of claim 19, wherein said top cover means is movably connected to said wall means of body unit by means of a hinge.

23. The improvement of claim 19, wherein said bottom cover means is movably connected to said body unit by means of a hinge.

* * * * *